(12) United States Patent
O'Young et al.

(10) Patent No.: US 6,555,720 B1
(45) Date of Patent: Apr. 29, 2003

(54) METHOD AND SYSTEM FOR PRODUCING 1,4-BUTANEDIOL

(75) Inventors: Lionel O'Young, Redwood City, CA (US); Kazuyuki Ookubo, Yokkaichi (JP); Nobuo Toratani, Kurashiki (JP); Hiroshi Iwasaka, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/560,453

(22) Filed: Apr. 28, 2000

(51) Int. Cl.$^7$ ............... C07C 27/00; C07C 27/02; C07C 31/18; C07C 33/02; C07C 29/00; C07C 27/26; C07C 29/74

(52) U.S. Cl. ............. 568/858; 568/857; 568/865; 568/868

(58) Field of Search .................. 568/858, 857, 568/865, 868

(56) References Cited

U.S. PATENT DOCUMENTS

| | | | |
|---|---|---|---|
| 3,929,915 A | 12/1975 | Cumbo et al. | 260/635 E |
| 4,010,197 A | 3/1977 | Toriya et al. | 260/491 |
| 4,062,900 A | 12/1977 | Tanabe et al. | 260/637 R |
| 4,091,041 A | 5/1978 | Smith | 568/865 |
| 4,150,239 A | 4/1979 | Tanabe et al. | 560/244 |
| 5,397,439 A | 3/1995 | Kandori et al. | 203/31 |
| 5,981,810 A | 11/1999 | Okuyama | 568/868 |

FOREIGN PATENT DOCUMENTS

| | | | | |
|---|---|---|---|---|
| GB | 2003144 A | | 3/1979 | C07D/307/08 |
| GB | 2003144 A | * | 3/1979 | C07D/307/08 |
| JP | 52007909 A | | 1/1977 | C07C/31/18 |
| JP | 52065209 A | | 5/1977 | C07C/21/20 |
| JP | 11-106359 | | 4/1999 | C07C/31/20 |
| JP | 11116515 A | | 4/1999 | C07C/31/20 |

* cited by examiner

*Primary Examiner*—Johann Richter
*Assistant Examiner*—Elvis O. Price
(74) *Attorney, Agent, or Firm*—Dorsey & Whtiney LLP

(57) ABSTRACT

A method and system for producing 1,4-butanediol (1,4-BG), and optionally additionally tetrahydrofuran (THF), that promotes more efficient usage of water ($H_2O$) is provided. In one aspect, the method is comprised of supplying at least one feed stream including 1,4-diacetoxybutane (1,4-DAB), 1,4-hydroxyacetoxybutane (1,4-HAB) and $H_2O$ to at least one reactor. 1,4-DAB, 1,4-HAB and $H_2O$ are reacted in the reactor to produce at least one effluent stream that includes 1,4-BG, 1,4-HAB, $H_2O$, unreacted 1,4-DAB and acetic acid. The effluent stream is supplied to a separation system having one or more separators where at least a portion of the 1,4-HAB is removed from the effluent stream and recycled back to the reaction. Alternatively, 1,4-HAB may be supplied directly to the reactor as a feed stream, or a combination of feed stream and recycled 1,4-HAB may be used.

17 Claims, 13 Drawing Sheets

Total H2O = 78050 kg/hr
1,4-HAB to 1,4-BG ratio is 0.30
Water efficiency = 0.070

Total H2O = 26050 kg/hr
1,4-HAB to 1,4-BG ratio is 0.92
Water efficiency = 20.9%

Total H2O = 16224 kg/hr
1,4-HAB to 1,4-BG ratio is 1.83
Water efficiency = 32.0%

Total H2O = 20650 kg/hr
1,4-HAB to 1,4-BG ratio is 0.47
Water efficiency = 26.3%

Total H2O = 9356 kg/hr
1,4-HAB to 1,4-BG ratio is 1.03
Water efficiency = 41.7%

METHOD AND SYSTEM FOR PRODUCING 1,4-BUTANEDIOL

FIELD OF THE INVENTION

The present invention relates to a method and system for producing butanediol, and in particular 1,4-butanediol (1,4-BG). More specifically, the present invention relates to a method and system for producing 1,4-BG in a hydrolysis reaction wherein 1,4-hydroxyacetoxybutane (1,4-HAB) is utilized as a starting material or reactant which acts to shift the equilibrium of the hydrolysis reaction to reduce the amount of water ($H_2O$) required to carry out the hydrolysis reaction. Moreover, it leads to an overall optimum total operating cost which includes utility and capital cost considerations.

BACKGROUND OF THE INVENTION

Butanediols, and in particular 1,4-butanediol (1,4-BG), find wide use in the chemical industry. 1,4-BG is used for a variety of purposes, and notable examples of its utility include use as a raw material for the production of a number of chemicals such as for the production of polyester. A number of processes are conventionally utilized to produce 1,4-butanediol. Conventional methods generally employ a hydrolysis reaction to produce 1,4-butanediol. For example, butadiene is reacted in an acetoxylation reaction with acetic acid (AcOH) and Oxygen then further hydrogenated to form 1,4-diacetoxybutane (1,4-DAB). 1,4-DAB is then further reacted with water ($H_2O$) in liquid phase to produce 1,4-BG, 1,4-hydroxyacetoxybutane (1,4-HAB) and AcOH. Therefore, the product stream generally includes 1,4-HAB, AcOH, unreacted 1,4-DAB and various by-products. Purified 1,4-BG is typically recovered by multiple distillation steps. Typically, the 1,4-HAB and unreacted 1,4-DAB may be further reacted with $H_2O$ at different reaction conditions to form tetrahydrofuran (THF).

These conventional methods of producing 1,4-BG and additionally THF, are very energy intensive. Very large amounts of $H_2O$ are consumed in the hydrolysis reaction. One conventional method of reducing the amount of $H_2O$ used in the reaction is to employ more than one reaction/separation stage. An example of one illustrative embodiment of a prior art reaction system 10 is shown in FIG. 1a. Typically, multiple hydrolysis reactions are carried out in one or more reactors, and in FIG. 1a three reactor stages in series 12a–12c are shown, each having an associated separation stage 14a–14c. Large amounts of $H_2O$, along with AcOH are separated in the separation stages and then conveyed to a waste water treatment plant (not shown) where the waste is treated which usually includes the recovery of AcOH in an acetic acid purification section (not shown). The boiling point of $H_2O$ and AcOH are lower than our desirable product(s), and thus they are typically removed as the distillate from the distillation tower. Although a very large relative volatility exists (i.e. the separation is relatively easy), it is necessary to boil off all of the $H_2O$ and AcOH. Hence, a large amount of energy is consumed.

To reduce the total amount of fresh $H_2O$ consumption, an alternative embodiment of the system 10 may be used; where typically, fresh $H_2O$ will only be added to the last stage of the reactors (i.e. 12c) in series, as shown in FIG. 1b. Then, the $H_2O$ together with AcOH formed in this separator of the last stage reactor, is recycled back to the previous reactor, or alternatively a recycled back to both of the previous reactors, and further, $H_2O$ and AcOH formed in the separator of the middle stage reactor may also be recycled to the first reactor as shown in FIG. 1b. This typical recycling system increases the total amount of $H_2O$ consumption slightly, however we can reduce the amount of total fresh $H_2O$ consumption significantly, consequently we will lower the energy consumption at the AcOH purification section and reduce the loading on the waste water treatment plant. However, regarding the total energy consumption for the overall system 10, it is still dominated by the total amount of $H_2O$ usage in the reactors, as a large amount of energy is needed to vaporized the $H_2O$ and AcOH from the mixture in the separators.

To understand the relationship of $H_2O$ usage (and therefore energy consumption) to the amount of 1,4-BG and 1,4-HAB production, lets start with the simple case of a system having one reactor stage with no recycle stream or system. FIG. 2a shows the performance of such a prior art reaction system. The x-axis shows the amount of $H_2O$ usage in the reactor, while the y-axis shows the amount of 1,4-BG production (curve A) and the corresponding production of 1,4-HAB (curve B) for a fixed feed amount of 1,4-DAB (in this example 12,800 kg/hr of 1,4-DAB as feed). It clearly shown that to achieve a typical desirable yield of 1,4-BG to 1,4-HAB (i.e., 1,4-BG/1,4-HAB mix) of a ratio of say 6:1 (5929 kg/hr-1,4-BG and 988 kg/hr-1,4-HAB), a large amount of $H_2O$ is used, in this case 145,000-kg/hr $H_2O$. To determine the $H_2O$ efficiency of such as system, the amount of product, in this case 5929 kg/hr of 1,4-BG is divided by the total amount of $H_2O$ used (145,000 kg/hr) to arrive at a water efficiency of only 4.09%. This is illustrated in FIG. 2b where Curve I shows the production of 1,4-BG and Curve II is the water efficiency.

To reduce this amount of total $H_2O$ usage and/or energy consumption, one method used is to introduce an additional number of reactors to the system 10, as mentioned above. Moreover, since the system is employing multiple reactor stages, it is possible to reduce the total amount of fresh $H_2O$ by recycling the $H_2O$ from the separators to one or more of the previous reactors. However, in doing so, there is a very small penalty on the total amount of $H_2O$ usage.

There is another element that needs to be considered when determining the best overall performance of the system 10. This additional element is the capital cost of the system 10. For this hydrolysis reaction system, since it is an equilibrium reaction and the reaction conditions are close to equilibrium. Further, the amount of $H_2O$ flow in the system is almost equal to the total flowrate at the system due to the small value of equilibrium constant. Therefore, the amount of total $H_2O$ usage can be used as the measurement of the capital cost. This is because as the system uses more $H_2O$, the reactor size is greater, and consequently the capital cost of the system is higher.

While the amount of $H_2O$ usage, and thus the energy consumption or costs, associated with producing 1,4-BG and additionally THF are reduced by employing more reactor stages (i.e. reactors/separators) and $H_2O$ recycle streams, the capital costs increase with the addition of these units. The prior art system configuration employing three reactors/separators and two $H_2O$/AcOH recycle streams is desirable from both an energy and capital cost point of view. For the capital cost, although this prior art configuration uses two additional reactors as compared to the single reactor case, the total flow rate for the reactor system is significantly smaller than that for the single reactor case. Consequently, the size of the equipment is much smaller and this offsets the cost of the additional equipment necessary for the three-reactor configuration. Hence, in this instance the total capital cost for the three reactors with two $H_2O$/AcOH recycle streams is lower than that for the one reactor with no $H_2O$/AcOH recycle. However, there are many variables, constraints and tradeoffs between the energy costs and capital costs that must be considered.

Another technique that has been employed in the prior art is to recycle 1,4-HAB produced in the reaction back to the reactor. For example, Japanese Patent No. 55-16489 discloses recycling AcOH, diols and/or 1,4-HAB to a reactor. Japanese Patent No. 11-169435 describes recycling an effluent stream including 1,4-HAB to one or more reactors and focuses on reducing the amount of 1,4-HAB recycle. While these methods have provided an improved process, further improvement is desirable. Moreover, in these prior art patents it is believed that the desirable product is only 1,4-BG. Consequently, 1,4-HAB is considered as a waste and thus recycling it will be desirable. Accordingly, it would be highly desirable to provide a method and system for producing 1,4-BG, and optionally additionally THF, which promotes the more efficient usage of $H_2O$ and is capable of minimizing both the operating or energy costs of production and the capital expense of the system.

SUMMARY OF THE INVENTION

Accordingly, in summary, it is an object of the present invention to provide a method and system for producing 1,4-BG, and optionally additionally THF, in a hydrolysis reaction of 1,4-DAB.

It is another object of the present invention to provide a method and system for producing 1,4-BG, and optionally additionally THF, in a hydrolysis reaction where the operating or energy costs and/or capital costs associated with the system are reduced in comparison to the prior art systems.

It is another object of the present invention to provide a method and system for producing 1,4-BG, and optionally additionally THF, that promotes more efficient usage of $H_2O$.

The inventors have discovered that the hydrolysis reaction may be shifted to favor the production of 1,4-BG with a significant reduction in the amount of $H_2O$ required to carry out the hydrolysis reactions. More specifically, the present invention provides a method and system for producing 1,4-BG in a hydrolysis reaction wherein 1,4-HAB is utilized as a starting material or reactant. The inventors have discovered that utilizing 1,4-HAB as a reactant in the hydrolysis reaction "shifts" the equilibrium of the reactions to favor the formation of 1,4-BG. The equilibrium of the hydrolysis reaction may be shifted according to the present invention by providing 1,4-HAB to the reactor in a feed stream, or by recycling at least a portion of 1,4-HAB that is produced by the hydrolysis reaction back to the reactor, or by using a combination of both. The method and system of the present invention promotes a number of significant advantages. For example, utilizing 1,4-HAB as a reactant in the hydrolysis reaction to shift the equilibrium of the reaction significantly reduces the amount of $H_2O$ required to carry out the hydrolysis reaction. Furthermore, this significant reduction in the usage of $H_2O$ can be realized with system configuration comprised of less number of reactor/separators.

Accordingly, in one aspect, the present invention provides for a method of producing 1,4-BG in a hydrolysis reaction, comprising the steps of: supplying at least one feed stream including 1,4-DAB, 1,4-HAB and $H_2O$ to at least one reactor. 1,4-DAB, 1,4-HAB and $H_2O$ are reacted in the reactor to produce at least one effluent stream that includes 1,4-BG, 1,4-HAB, $H_2O$, unreacted 1,4-DAB and AcOH. The effluent stream is supplied to a separation system having one or more separators where preferably at least a portion of the 1,4-HAB is removed from the effluent stream and recycled back to the reactor. Alternatively, 1,4-HAB may be supplied directly to the reactor as a feed stream, as opposed to being recycled from the process itself. In yet another embodiment, 1,4-HAB is supplied using a combination of recycling a portion and providing a portion in the feed stream. However, it is preferred to recycle at least a portion of the 1,4-HAB since it is a by-product of the reaction, and thus is readily available.

Of particular advantage, the system and method of the present invention is carried out such that the following equations are satisfied. Specifically, the inventors have developed upper (Max) and lower (Min) operating bounds which factor in the capital costs and energy use of the system, and then an operating condition (Var) is selected between such bounds as shown in the following equations:

$$\text{Min} \leq \text{Var} \leq \text{Max} \tag{1}$$

$$\text{Preferably Min'} < \text{Var} < \text{Max} \tag{2}$$

$$\text{where Max}=(7.59D-0.76)/n \tag{3}$$

$$\text{Min}=(3.79D-2.00)/n \tag{4}$$

$$\text{Min'}=(3.79D-1.46)/n \tag{5}$$

$$\text{and Var}=B/A \tag{6}$$

$$\text{and } D=174(C)/90(A) \tag{7}$$

and where A is the feed rate of 1,4-DAB to the reaction system in kg/hr;

B is the feed rate of fresh 1,4-HAB to the reaction system plus the total amount of 1,4-HAB recycled to the reaction system in kg/hr;

C is the amount of 1,4-BG produced by the reaction system, and n is the number of reactors within the reaction system.

In another aspect, the present invention provides a method of reducing the operating costs of a hydrolysis reaction to produce products including 1,4-BG wherein the cost of operating the hydrolysis reaction is defined in part by energy costs and capital costs. By using 1,4-HAB as a reactant, the equilibrium of the hydrolysis reaction is shifted toward increased production yield of 1,4-BG and decreased usage of $H_2O$ as compared to that in the absence of 1,4-HAB as a reactant. In this reaction, the energy costs are driven primarily by the $H_2O$ usage, and thus a reduction in the usage of $H_2O$ reduces the energy costs. Of further advantage, the reduction in the amount of $H_2O$ consumed in the hydrolysis reaction can provide a reduction in the capital costs of the system as the size of the reactors may be reduced.

In yet another aspect of the present invention, a hydrolysis system for producing products including 1,4-BG in a hydrolysis reaction is provided, comprising a reactor that receives reactants 1,4-DAB, $H_2O$, 1,4-HAB and reacts said reactants to produce an effluent stream including 1,4-BG, 1,4-HAB, $H_2O$, unreacted 1,4-DAB, and AcOH. A separation system receives the effluent stream and separates at least a portion of the 1,4-HAB from the effluent. Preferably a recycle stream is coupled to the separation system and conveys at least a portion of the 1,4-HAB back to the reactor as a reactant.

BRIEF DESCRIPTION OF THE DRAWINGS

Additional objects and features of the invention will become more clearly apparent from the following detailed description and appended claims when taken in conjunction with the drawings, in which:

DETAILED DESCRIPTION OF THE INVENTION

Figure 1A:
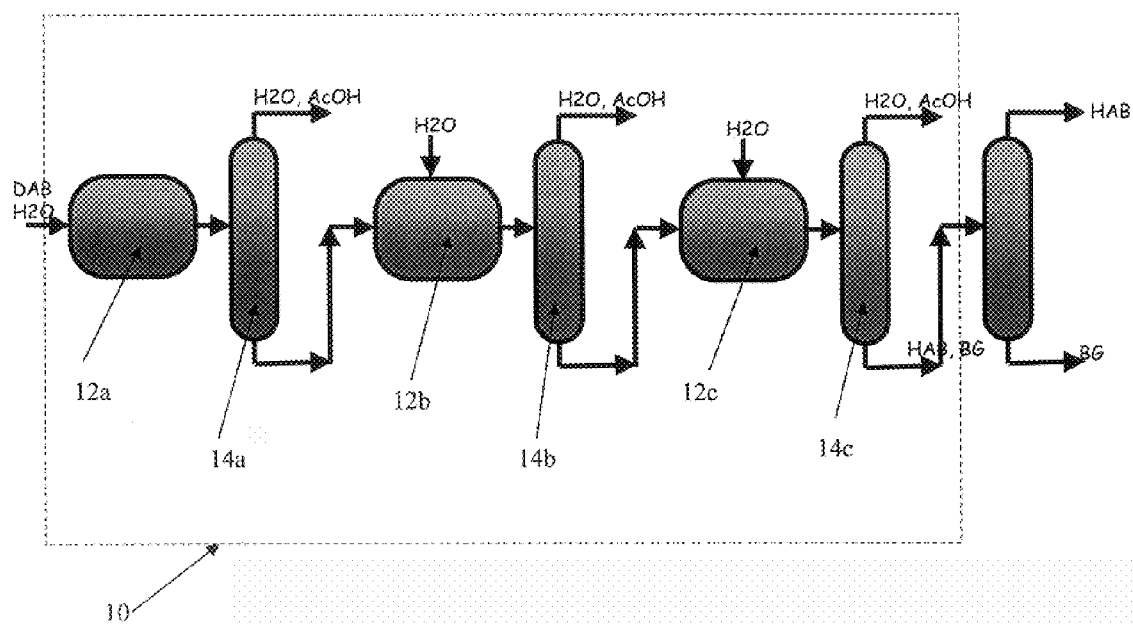
FIGS. 1a and 1b show a schematic diagrams of examples of two different a prior art systems for producing 1,4-BG.

The present invention provides a method and system for producing 1,4-BG, and optionally additionally THF. The inventors have discovered a method and system that significantly reduces the energy or operating costs and/or capital expenditures associated with producing 1,4-BG, and optionally additionally THF. Specifically, the invention provides a system and method for producing 1,4-BG, and optionally additionally THF, wherein 1,4-HAB is provided as a feed starting material or reactant to the system. The addition of 1,4-HAB as a reactant causes a shift in the equilibrium of the hydrolysis reaction (described in detail below) such that the usage of $H_2O$ is reduced. Reducing the usage or mass flow rate of $H_2O$ reduces the energy costs of the system. As will be described in detail below, this method also reduces capital costs by providing a system configuration which may employ a combination of fewer reactors/separators and/or smaller sized equipment and still achieve a desirable yield of 1,4-BG, which compared to a prior art configuration would require multiple reactors to achieve a similar yield of 1,4-BG.

Of particular advantage, the system and method of the present invention is carried out such that the following equations are satisfied. Specifically, the inventors have developed upper (Max) and lower (Min) operating bounds which factor in the capital costs and energy use of the system, and then an operating condition (Var) is selected between such bounds as shown in the following equations:

$$Min \leq Var \leq Max$$

$$\text{Preferably Min'} < Var < Max \quad (2)$$

$$\text{where Max} = (7.59D - 0.76)/n \quad (3)$$

$$Min = (3.79D - 2.00)/n \quad (4)$$

$$Min' = (3.79D - 1.46)/n \quad (5)$$

$$\text{and Var} = B/A \quad (6)$$

$$\text{and } D = 174(C)/90(A) \quad (7)$$

and where A is the feed rate of 1,4-DAB to the reaction system in kg/hr;

B is the feed rate of fresh 1,4-HAB to the reaction system plus the total amount of 1,4-HAB recycled to the reaction system in kg/hr;

C is the amount of 1,4-BG produced by the reaction system, and n is the number of reactors within the reaction system.

Figure 2A:
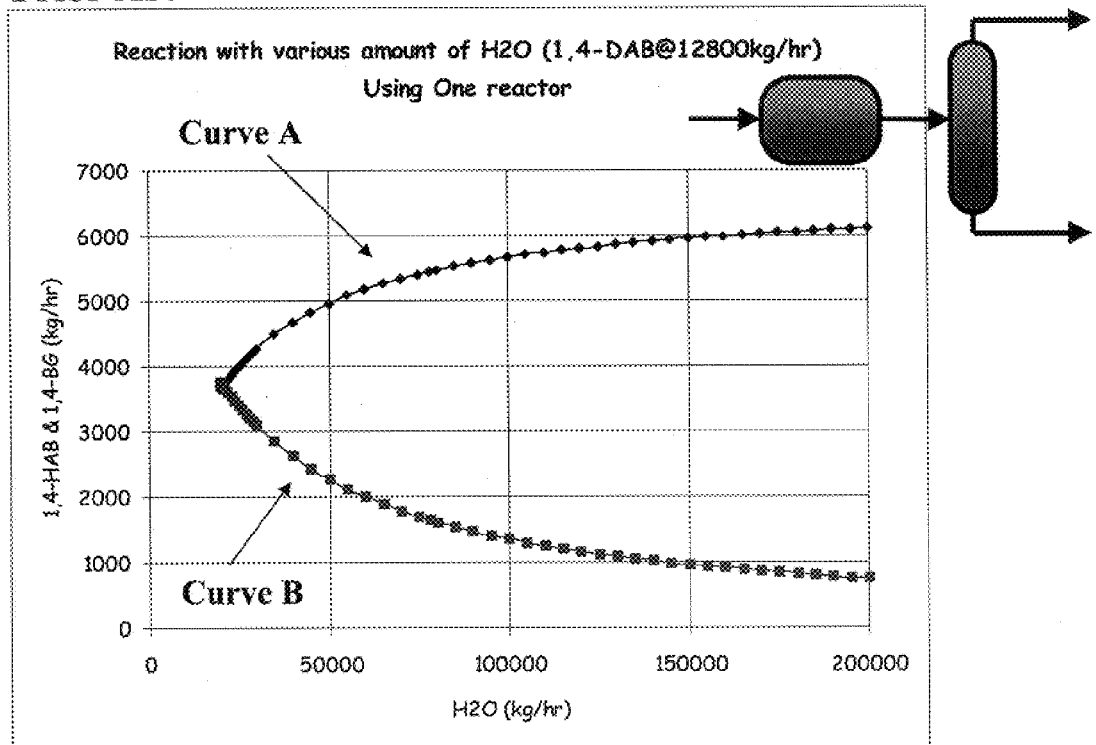
FIG. 2a is a plot of 1,4-BG production and 1,4-HAB production as a function of the total amount of $H_2O$ consumed for a prior art system employing one reactor stage.
Figure 2B:
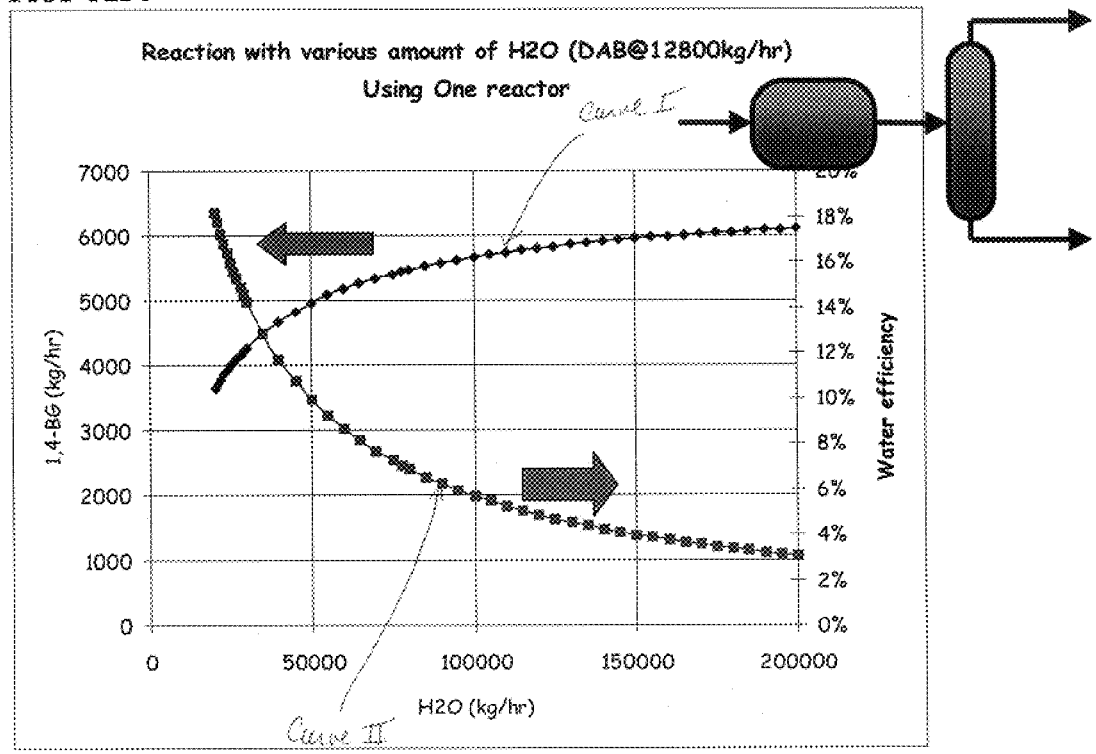
FIG. 2b is a plot of 1,4-BG production and the water efficiency as a function of the total amount of $H_2O$ consumed for a prior art system employing one reactor stage.

The advantages of this criteria can be better appreciated with consideration of "the water efficiency" of the reaction system. Consider the one reactor system of the prior art, the performance of which is shown in FIG. 2b. The water efficiency is defined as the amount of 1,4-BG formed (i.e. the product) divided by the total amount of $H_2O$ consumed in the reactor. From FIG. 2b, we can clearly see that the water efficiency is very high at the low conversion condition (i.e. where the yield of 1,4-BG is small). However, when the yield of 1,4-BG increases, the water efficiency drops very significantly. As described earlier, the $H_2O$ usage in this system is the primary contributor to the energy and capital costs. Hence it is highly desirable to keep the system operating at the high water efficiency condition while producing a desirable yield of the 1,4-BG product. According to the present invention, based upon the equilibrium constants of the reaction, relatively high water efficiency is promoted when the operating condition (Var) is between the upper (Max) and lower (Min) bounds. When the operating condition is below the lower bound (i.e. Var<Min) then the reaction system is using too much $H_2O$, hence both the energy and capital cost are not minimized. This is because when the operating condition is below the lower bound, the 1,4-HAB recycle amount is low thereby resulting in a low 1,4-HAB to 1,4-BG ratio at the outlet of the final reactor, which is undesirable.

Of further advantage, the above equations also account for the capital costs of the system. Specifically, when the operating condition (Var) is greater than the upper bound (Max), the reactor system design is using more capital than desired; i.e. the system is recycling too much 1,4-HAB into the reactor system. In doing so, of course we can achieve a very high energy efficiency but the penalty on the capital cost and the operating cost for separating 1,4-HAB is to large. Therefore, the system should lower its water efficiency in consideration of the overall system economics. Thus, the equations of the present invention provide for the selection of an optimized operating range between the upper and lower bounds.

Of particular advantage, providing 1,4-HAB as a reactant or starting material, either as a fresh feed stream, via a recycle stream, or by a combination of both, wherein the above equations are satisfied, improves the reaction system as indicated by a reduction in the amount of $H_2O$ consumed in comparison to same number of reactors/separators in a reaction system that does not employ 1,4-HAB as a starting material. Consequently, due to the reduction of $H_2O$ achieved by the invention, and the associated reduction in the total volumetric flowrate of the reactor system, we also reduce the size of the reaction system, which lowers the capital cost requirement of the reaction system. Additionally, the present invention employing 1,4-HAB as a starting material or reactant provides the opportunity for capital-energy cost tradeoff considerations, which allows one to tailor the system for the best overall total cost. Thus, it is possible to reduce the number of reactors, together with the $H_2O$ separator, with the expense of a slight increase in $H_2O$ consumption and hence a slight increase in energy cost and equipment size; however, there will be a reduction in the number of equipment units. In any event, the present invention provides a significant reduction in the total cost of the reaction system as compared to the prior art configurations.

Figure 2C:
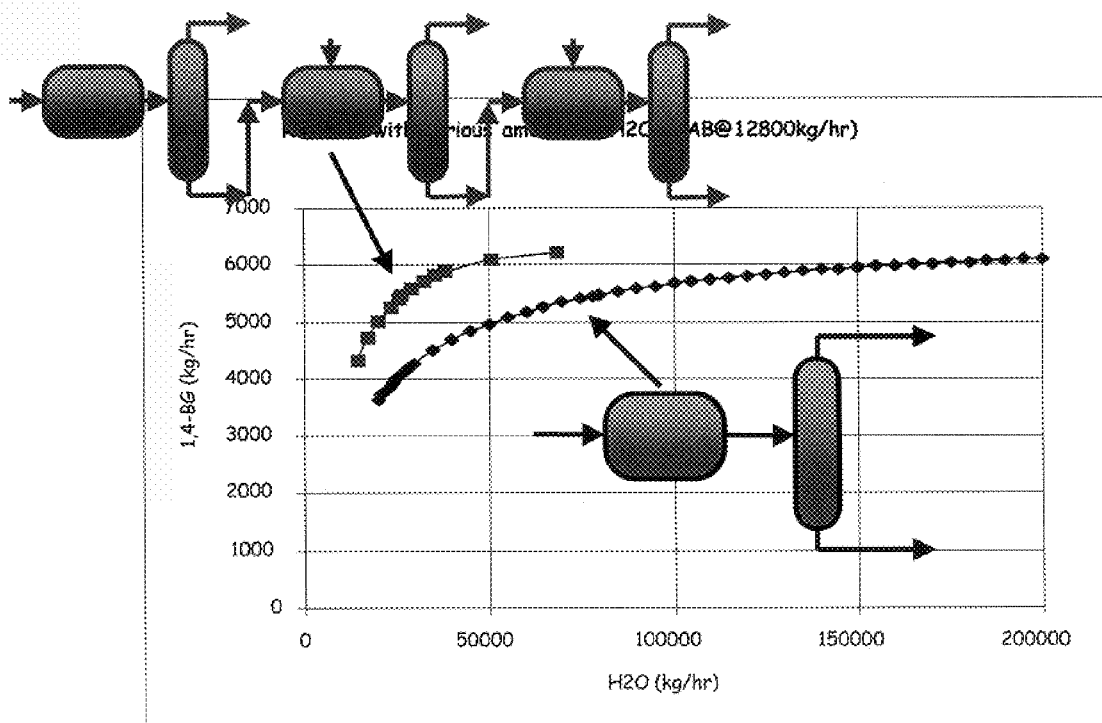
FIG. 2c is a plot of 1,4-BG production as a function of the total amount of $H_2O$ consumed for two prior art systems; namely, one employing one reactor stage, and the other employing three reactor stages.

This is illustrated in FIG. 2c which shows a comparison of performance of a prior art one-reactor system to a prior art three-reactor system. Clearly, the amount of $H_2O$ usage for the three reactors system is much lower than that of the one reactor system for an equivalent yield of product. However, the trade-off here is that additional equipment is needed to carry out the reaction using the three reactor system. For our invention, the important point is that both configurations exhibit the same shape of performance curve i.e. the curve has a steep slope in the beginning and then is asymptotic at high amounts of $H_2O$ usage. This means the water efficiency for both configurations are very high at the beginning when the yield of 1,4-BG is low, and then decreases as large amounts of $H_2O$ are consumed as the yield of 1,4-BG increases. The inventors have discovered that this behavior is not a coincidence, but that this shape of curve will be true for any system configuration since it is controlled by the equilibrium of the reaction chemistry. Given this discovery, then it follows that the only aspect that the equipment (i.e. topology and capital) configuration can control on the performance curve is how quickly the curve will move up to its asymptotic value (which is controlled by the overall material balance of the system). This is shown for example, in FIG. 2c where the three-reactor configuration has a steeper curve than the one-reactor configuration.

A portion of the hydrolysis reactions to produce 1,4-BG and THF are shown in Table 1 below. The main reaction I is a two step reaction where in the first step I-1, 1,4-DAB is reacted with $H_2O$ to produce 1,4-HAB with a by-product of AcOH. In the second step I-2, the 1,4-HAB further reacts with the $H_2O$ to produce 1,4-BG and AcOH. Many secondary side reactions also occur (not shown). THF can be formed by using either 1,4-HAB or 1,4-BG as reactants as shown in reactions II-1 to II-4:

TABLE 1

| | |
|---|---|
| I-1: | 1,4-DAB + $H_2O$ <==> 1,4-HAB + AcOH k1 = 0.66 |
| I-2: | 1,4-HAB + $H_2O$ <==> 1,4-BG + AcOH k2 = 0.16 |
| II-1: | 1,2-DAB + $H_2O$ <==> 1,2-HAB + AcOH |
| II-2: | 1,2-HAB + $H_2O$ <==> 1,2-BG + AcOH |
| II-3: | 1,4-HAB <==> THF + AcOH |
| II-4: | 1,4-BG <==> THF + $H_2O$ |

The main reaction I is a reversible reaction and typically will be run at or near equilibrium condition. The inventors have determined that the equilibrium constant (k1) for the first step I-1 is much larger than the equilibrium constant (k2) for the second step I-2, in fact it is roughly four times larger. Thus, a much greater amount of $H_2O$ is necessary to form 1,4-BG from 1,4-HAB, than to form 1,4-HAB from 1,4-DAB. Accordingly, the present invention acts to shift the equilibrium of the main reaction such that the amount of 1,4-HAB available to form 1,4-BG is increased which in turn decreases the amount of $H_2O$ needed to carry out the reaction. Consequently, if the desirable product has a high 1,4-BG to 1,4-HAB ratio (1,4-BG/1,4-HAB), then the amount of $H_2O$ consumed will be very high. To reduce the total amount of $H_2O$ consumed, we can shift the product equilibrium by lowering the 1,4-BG/1,4-HAB ratio at the outlet of the final separator, i.e. the product mix, thereby utilizing more 1,4-HAB in the reaction but still increasing the total amount of product yield since the net amount of 1,4-BG formed is kept the same.

Shifting the equilibrium is accomplished according to the present invention by employing 1,4-HAB as a feed reactant or starting material to the system and by maintaining an operating condition (Var) between the upper (Max) and lower (Min) bounds. The inventors have found that when satisfying the equations 1 through 7 above, a certain composition ratio of 1,4-HAB to 1,4-BG at the outlet of the final reactor within the system will be maintained. This composition is such that the ratio of 1,4-HAB/1,4-BG in weight percent at the outlet of the final reactor in the system is in the broad range, independent of the number of reactors n, of approximately 0.4 to 2.0, more preferably in the range of approximately 0.6 to 1.5. 1,4-HAB may be supplied as a fresh reactant to the system; however, since 1,4-HAB is produced from the reaction of 1,4-DAB and $H_2O$, it is preferred that at least a portion of the 1,4-HAB be supplied from the products of and $H_2O$, it is preferred that at least a portion of the 1,4-HAB be supplied from the products of the reaction itself via a recycle stream, and optionally, a combination of both fresh and recycled HAB may be supplied to the reactor.

Figure 1B:
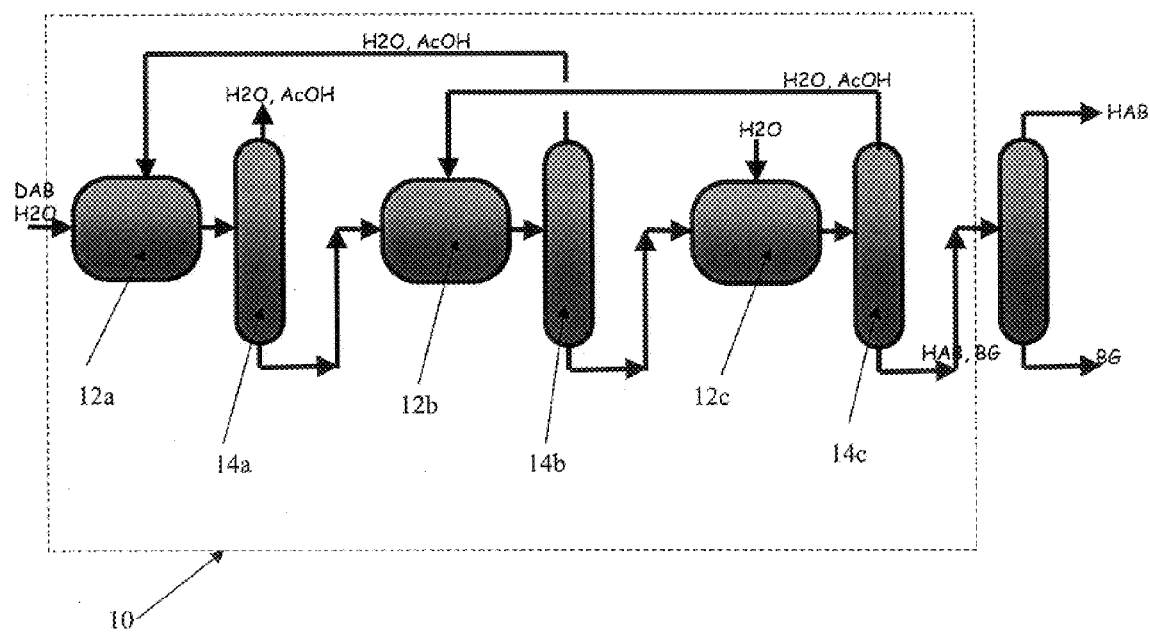
Figure 3A:
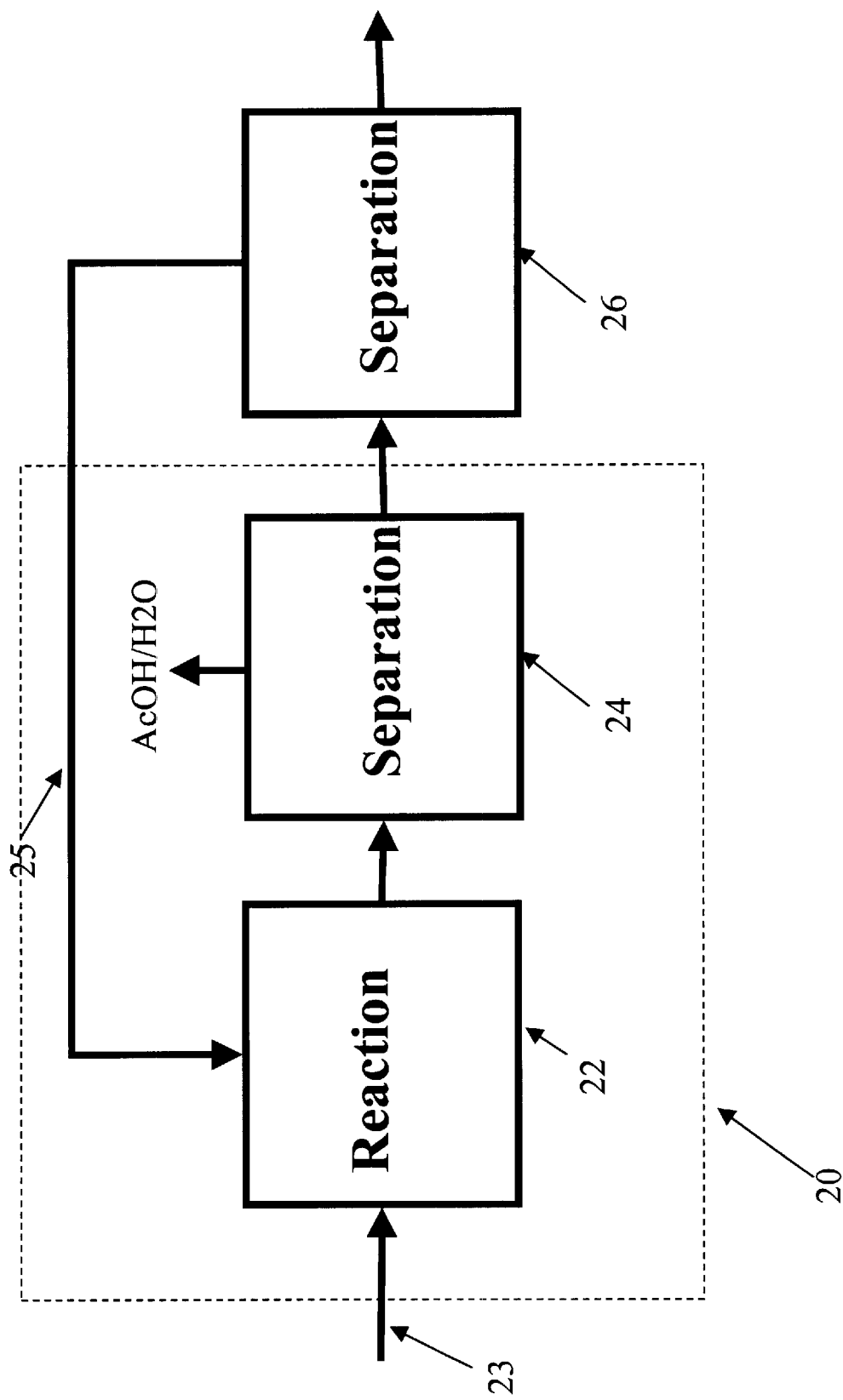
FIGS. 3a and 3b show simplified schematic diagrams of a reaction system for producing 1,4-BG according to two different embodiments of the present invention.
Figure 3B:
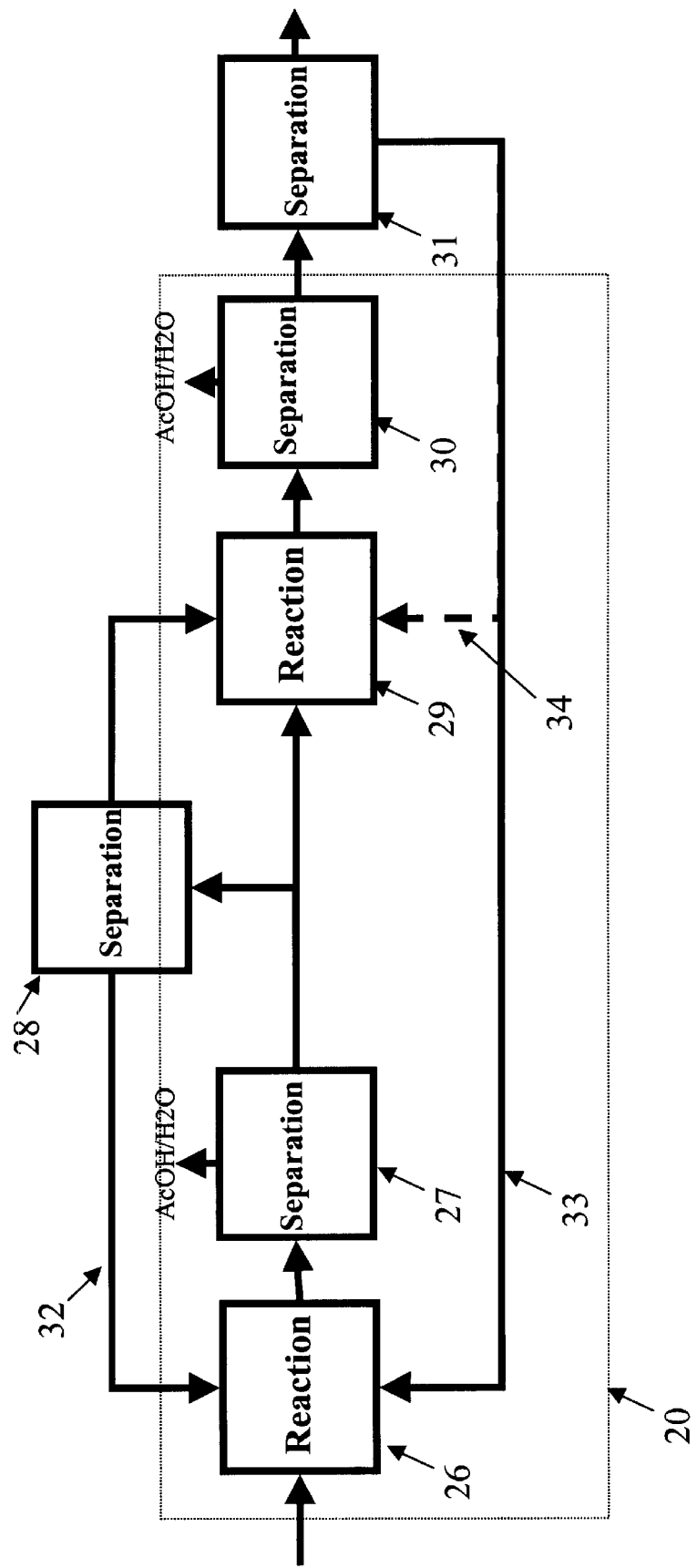

FIGS. 3a and 3b are simplified schematic drawings illustrating the hydrolysis reaction system 20 with 1,4-HAB recycle system according to two alternative embodiments of the present invention. In FIG. 3a, the reaction system 20 has one reaction stage which generally includes a reactor system 22 and a separation system 24 for removing $H_2O$ and AcOH. Outside the reaction system there is another separation system 26 which acts as a means for supplying 1,4-HAB to the reactor system 22. In the first embodiment shown in FIG. 3a, 1,4-HAB is supplied to the reactor system 22 via a recycle stream 25 which recycles 1,4-HAB from the separation system 26 to the reactor 22. Optionally, 1,4-HAB may also be supplied to the reactor system 22 as a fresh reactant via the feed inlet 23. In the second embodiment shown in FIG. 3b, a two stage reactor system is shown. Reaction systems 26 and 29 are in series and are each coupled to an associated $H_2O$ and AcOH separation system 27 and 30, respectively. 1,4-HAB is supplied to one or both of the reactors 26 and 28 by one or more recycle streams 32 and 33 and optionally 34 which in the exemplary embodiment recycles 1,4-HAB from each of the separation systems 28 and 31 to the first reactor 26. Alternatively, 1,4-HAB may also be recycled to the second reactor 29. While the reactors and separation systems are shown simply as a block diagram, it is to understood that such systems may employ any number of suitable components or unit operations as appropriate. For example, the separation systems 27, 28, 30 and 31 may employ any single or combination of suitably adapted separation equipment, such as direct or indirect separation sequence, vaporization, employing single or multiple stage distillation under reduced, normal or high pressures as applicable, or any other suitable means.

Figure 4:
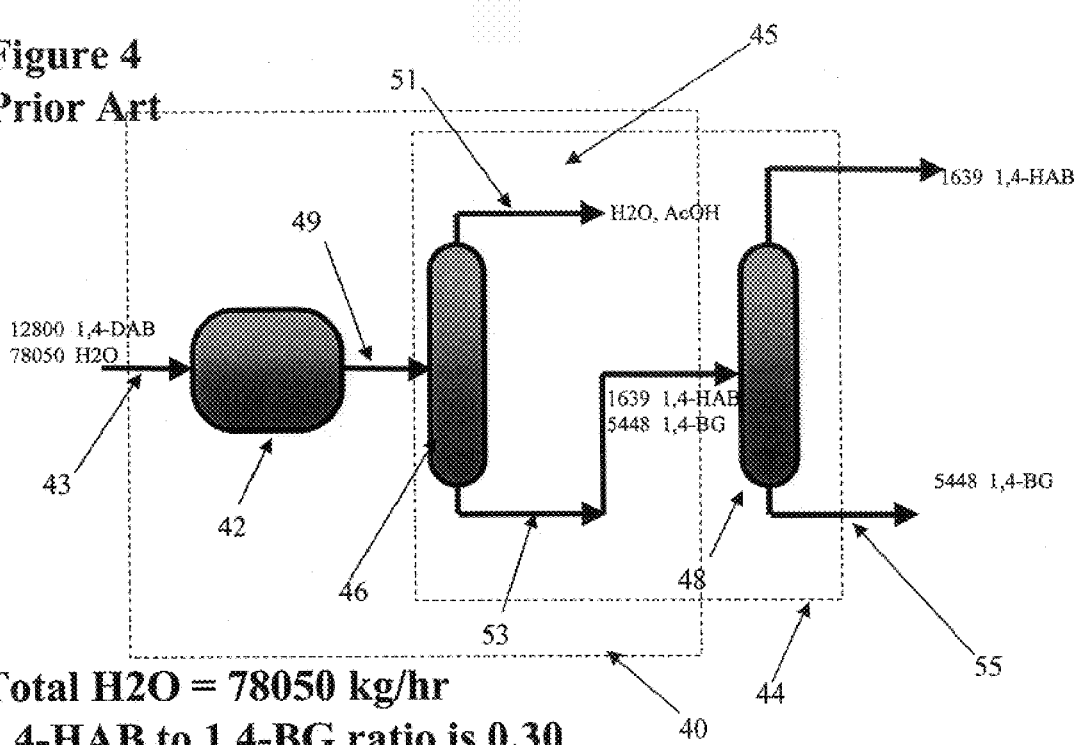
FIG. 4 is a schematic diagram of a prior art system showing its water efficiency.
Figure 5A:
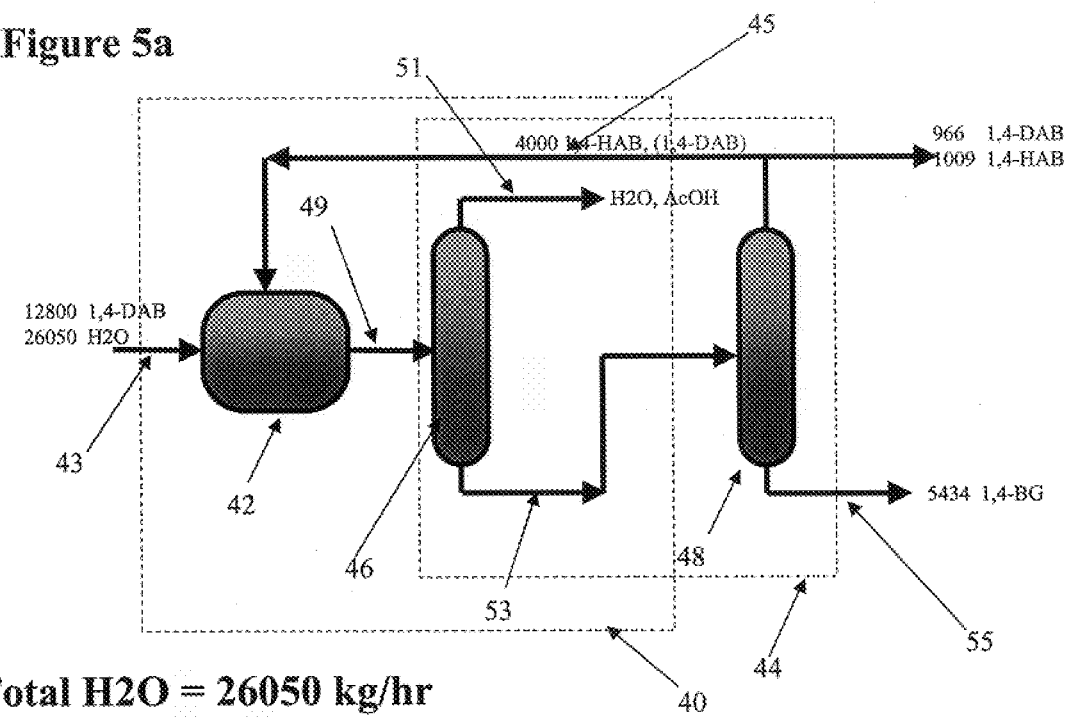
FIGS. 5a and 5b are schematic diagrams of reaction systems for producing 1,4-BG according to one embodiment of the present invention, and illustrating changes in the water efficiency.
Figure 5B:
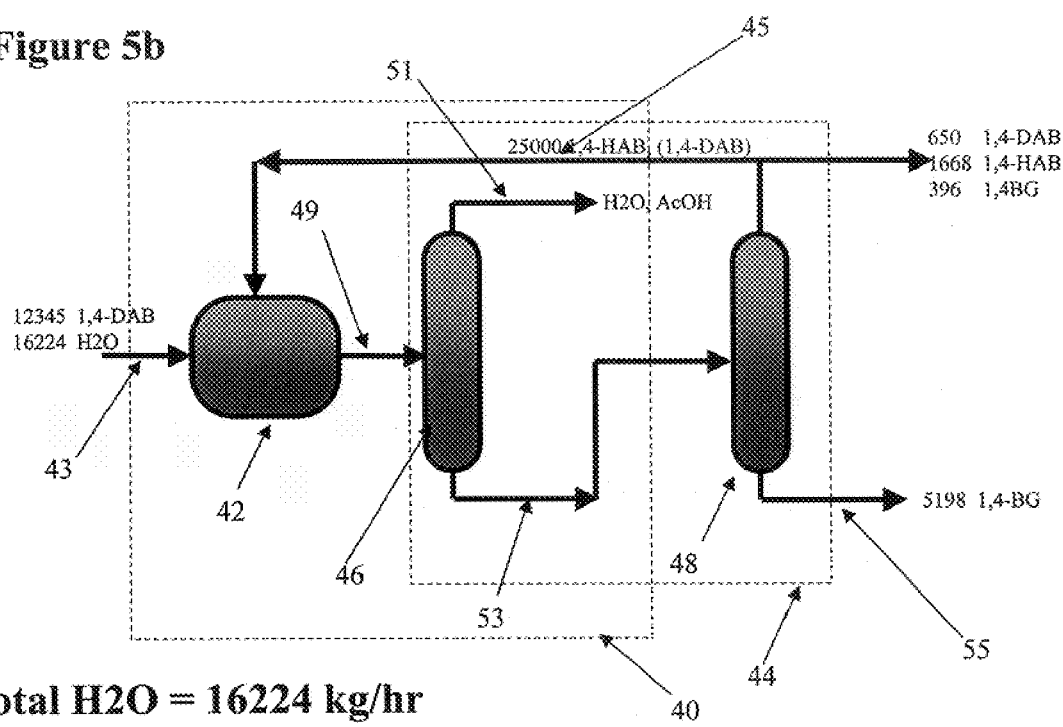

The method and system of the present invention are described in greater detail with reference to FIGS. 5a and 5b and compared to FIG. 4. FIGS. 5a and 5b show two embodiments of the present invention, while FIG. 4 shows a prior art system and will illustrate the significant impact of the recycle of 1,4-HAB according to the present invention as described below. In FIG. 5a the reaction system 40 is a one or single stage reactor system and generally includes one reactor 42, a separation system 44 and a means for conveying 1,4-HAB to the reactor 42. Examples of flowrates of the constituents are also shown on the figure to assist in the teaching. The type of reactor 42 utilized in any of the described embodiments is not particularly limited and may be comprised of any number of reactor configurations suitably adapted for carrying out a hydrolysis reaction. Preferably the reactor 42 is comprised of a fixed bed type reactor. The type of separation system 44 is also not particularly limited and may be comprised of any number of suitable separation units. Preferably, the separation system 44 comprises one or more distillation columns. In the exemplary embodiment shown in FIG. 5a the separation system 44 includes a first distillation tower 46 and second distillation tower 48. The means for conveying 1,4-HAB may take a variety of forms, and is typically comprised of a feed inlet 43, a recycle stream 45, or a combination of both. FIG. 5a shows one illustrative example wherein 1,4-HAB is supplied to the reactor 42 via the recycle stream 45. Furthermore, the recycle stream 45 may include a split stream for directing a portion of the recycled 1,4-HAB for other purposes. The recycle stream 45 will also typically include a small amount of unreacted 1,4-DAB.

To carry out the method of the present invention, reactants 1,4-DAB, 1,4-HAB and $H_2O$ are supplied to the reactor 42. The reactants undergo hydrolysis and produce a reaction effluent stream 49 at the outlet of the only, and in this case final, reactor 42. The effluent stream 49 includes 1,4-BG, 1,4-HAB, unreacted 1,4-DAB, AcOH and $H_2O$. The effluent stream is conveyed to the first distillation tower 46 wherein $H_2O$ and AcOH are separated from the effluent stream and purged from the top or upper portion of the tower 46 via purge stream 51, and then conveyed typically to an acetic acid recovery (purification) section, and then sent to a wastewater treatment plant (not shown). The bottom product 53 from the first distillation tower 46 is conveyed to the second distillation tower 48 wherein at least a portion of the 1,4-HAB is separated from the final bottom product 55 and recycled back to the reactor 42 via recycle stream 45 from the top or upper portion of the tower 48. The final product is removed from the bottom of the tower 48 in product stream 55. The product stream 55 is comprised primarily of 1,4-BG, and also includes some 1,4-HAB, a small amount of unreacted 1,4-DAB and some heavy boilers. The total amount of $H_2O$ consumed in this example is about 26050 kg/hr.

In great contrast, FIG. 4 shows a hydrolysis system with one reactor design with no 1,4-HAB added to the reactor 42, either from the fresh feed or from the recycle of the reactor effluent stream. For comparison with the values on FIGS. 5a and 5b the flowrates of the constituents are also shown on FIG. 4. To produce the equivalent amount of 1,4-BG product and 1,4-HAB as shown in FIG. 5a, the amount of $H_2O$ usage is 78050 kg/hr in the prior art system shown in FIG. 4. This amount is roughly 3 times greater than the $H_2O$ consumed in the configuration of the present invention shown in FIG. 5a. In other words, the energy consumption of the prior art system shown in FIG. 4 is about three times as that of the present invention. Moreover, the size of the equipment utilized in the prior art system will also be roughly three times greater in volume in order to accommodate the larger flowrate of $H_2O$.

In comparison of the system configurations in FIG. 4 to FIGS. 5a and 5b, there is also another important aspect. That is, the overall material balance for both systems shown in FIGS. 5a and 5b are identical with respect to the conversion of 1,4-DAB to 1,4-BG. The amount of fresh 1,4 DAB consumed is 12,800 kg/hr. Also in all three cases, approximately 5440 kg/hr of 1,4-BG is made. But the overall conversion is higher for the system configuration in FIG. 4 than FIGS. 5a and 5b. This is due to equilibrium behavior of the main reaction I-1, as the amount of 1,4-HAB recycle increases, the overall conversion of 1,4-DAB will be reduced per pass. Fortunately, 1,4-DAB can be used as a raw material in producing THF or may be recycled back to this reaction via a THF reactor (not shown).

While the method and system of the present invention as illustrated in FIG. 5a provides a significant improvement in the water efficiency as compared to the prior art system shown in FIG. 4, further improvement is provided by the present invention. Referring again to FIG. 5a, the 1,4-HAB to 1,4-BG ratio at the outlet of the final reactor (at point 49) is 0.92. This value is within the cited range of the invention of 0.4 to 2.0; however, as noted above, this range does not factor in the number of reactors of the reaction system. The number of reactors is factored into the equation 1 to 7 above, and thus the system can be further improved by applying equations 1 to 7 to the conditions in FIG. 5a. Doing so provides the following results:

From FIG. 5a
A=12,800 kg/hr—the feed rate of 1,4-DAB,
B=0 kg/hr—the feed rate of 1,4-HAB
+4000 kg/hr—the amount of 1,4-HAB recycled to the reactor(s),
=4000 kg/hr
C=5434 kg/hr—the amount of 1,4-BG produced,
n=1—the number of reactors.

Given the above values, D is calculated according to equation 7, to give 0.814. Given the value of D, Max, Min and Min' are calculated from equations 3 to 5 to give: Max=5.47 and Min=1.11 and Min'=1.65. Then Var is calculated from equation 6 to give 0.313. Finally, the condition of equations 1 and 2; namely Min≦Var≦Max, and preferably Min'<Var<Max are considered. As we can see, in this example that Var is below the Min value, and thus this reaction system is not optimized. The amount of 1,4-HAB should preferably be increased to at least the value of the Min, which in this example is an increase in the 1,4-HAB recycle amount of about 5.3 times, or to at least approximately 22,000 kg/hr. FIG. 5b illustrates the same reaction of the system of FIG. 5a, except that the amount of 1,4-HAB recycle (i.e. variable B) has been increased to 25,000 kg/hr. Applying equations 1 through 7 to the values of A, B, C and n shown on FIG. 5b results in a Min' of 1.63, a Min of 1.09, a Max of 5.42 and a Var of 2.03. Thus the condition of Min≦Var≦Max, and preferably Min'<Var<Max are satisfied. This indicates that this reactor system achieves a good balance between the energy and capital costs. This is also demonstrated by an increase in the water efficiency. The reaction system of FIG. 5b has a water efficiency of about 32% as compared to the reaction system of FIG. 5a with a water efficiency of about 20.9%. However, it is important to note that while the inventive system of FIG. 5b is preferred, the inventive system of FIG. 5a is still much more water efficient than the prior art system shown in FIG. 4 with a water efficiency of only about 7%.

Figure 6A:
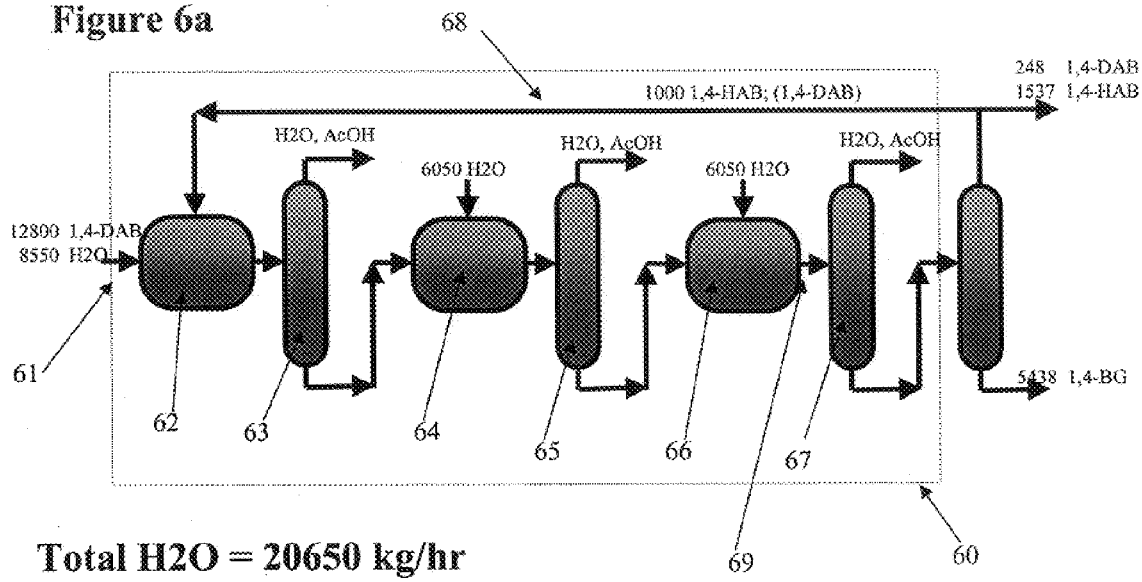
FIGS. 6a and 6b are schematic diagrams of reaction systems for producing 1,4-BG according to another embodiment of the present invention, and illustrating changes in the wafer efficiency.
Figure 6B:
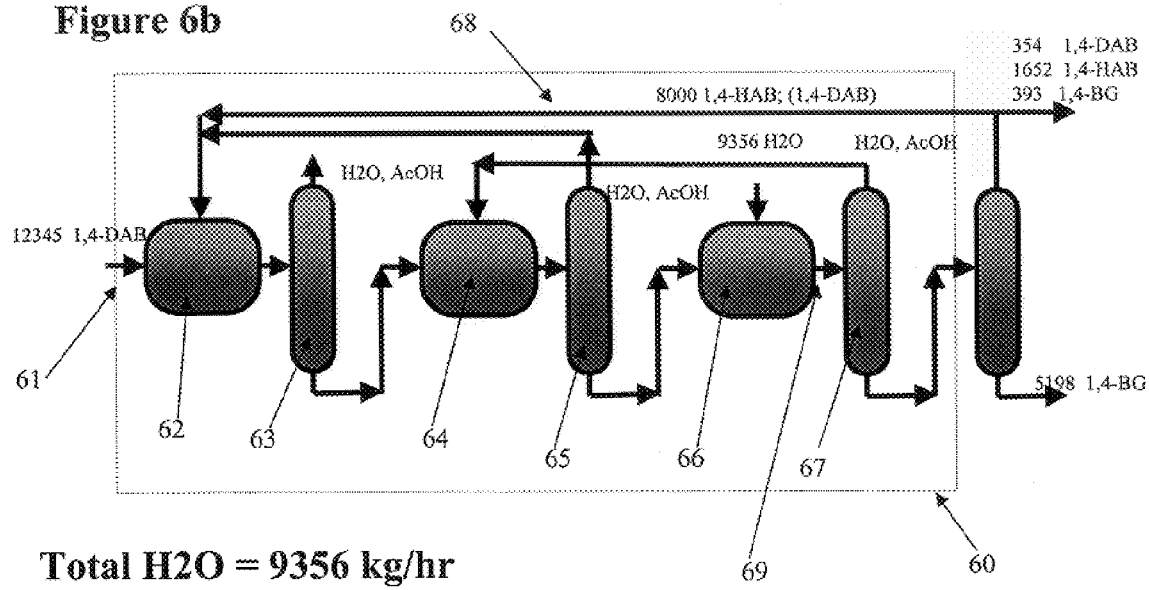

The method and system of the present invention may employ one or more reactors. Such an alternative embodiment is shown in FIGS. 6a and 6b, where the hydrolysis system 60 is a three reactor stage system having three reactors 62, 64 and 66, in series, each having an associated separation system 63, 65 and 67. According to the method of the present invention, 1,4-HAB is supplied as a reactant to the first reactor 62, and optionally, additionally to any one of, or to any combination of, the additional reactors. Again, the 1,4-HAB may be supplied directly to the reactors, or may be supplied from a recycle stream, or by a combination of both. As shown in the exemplary embodiments of FIGS. 6a and 6b, 1,4-HAB is supplied to the first reactor via recycle stream 68. For example, where a prior art system such as a three stage reactor system is in use, one or more 1,4-HAB recycle streams may be added to recycle 1,4-HAB as a feed reactant in accordance with the present invention, thereby "retrofitting" the prior art system such that it now operates according to the method of the present invention.

$H_2O$ is supplied to each of the reactors. The $H_2O$ may be supplied as fresh $H_2O$ as shown in FIG. 6a, or alternatively may be recycled from the downstream separation system as shown in FIG. 6b. For example, $H_2O$ purged from distillation tower 67 may be recycled to the first reactor 62 or the second reactor 64, or both.

Referring again to FIG. 6a, the 1,4-HAB to 1,4-BG ratio at the outlet of the final reactor is 0.47, which is within the broad recited inventive range of 0.4 to 2.0. The water efficiency of the reaction system in FIG. 6a is about 26.3%, well above the prior art systems. However, as described above, the efficiency of the reaction system may be further improved by applying equations 1 through 5 to determine the preferred recycle rate of 1,4-HAB (i.e. variable B).

Accordingly, referring again to FIG. 6a, the values of A, B, C and n are 12,800 kg/hr, 1000 kg/hr, 5438 kg/hr and 3, respectively. The value D is calculated from equation 7 to yield 0.82. The values of Min, Min' and Max are calculated by equations 3 to 5 and give 0.370, 0.551 and 1.825, respectively. The operating condition Var is calculated from equation 6 and yields 0.078. Thus, the equations 1 and 2 are not satisfied; as the value of Var is below the Min and Min' values. To satisfy this condition, the value of Var is increased by at least about 7 times to equal the Min or Min' value. Consequently, the 1,4-HAB recycle amount is increased by at least 7 times to give a recycle rate of at least 7000 kg/hr.

FIG. 6b illustrates a reaction system where the 1,4-HAB recycle rate is increased to 8000 kg/hr. In this embodiment the water efficiency is increased to about 41.7%, and equations 1 and 2 are satisfied indicating a good balance between the energy and capital costs.

In general, 1,4-DAB is used as a starting material and may be obtained from reacting butadiene with AcOH and oxygen and then hydrogenated to form 1,4-DAB. The hydrolysis reaction may be carried out under a variety of conditions which are conventional and well known in the art for hydrolysis reactions. It is preferred to employ a catalyst for the hydrolysis reaction, such as a ion exchange resin. An ion exchange resin such as that described in Japanese patent no. JPA52-19610 is particularly useful as a catalyst. The amount of catalyst suitably employed in the present invention is not particularly limited and need be only that minimum amount necessary to provide the basis for at least that amount which exhibits desirable catalytic activity and selectivity at the selected reaction temperature and pressure. Preferably, the reactors are fixed bed reactors packed with the cation exchange resin, and the reactants are permitted to flow through the fixed bed reactor; however, the hydrolysis reaction is not limited to this example, and other reaction methods and equipment may be used. In one exemplary illustration, the hydrolysis reaction is usually carried out at a temperature in the range of approximately 40 to 100 degrees C, and preferably at approximately 50 degrees C. Of course it should be understood that the disclosed temperature ranges are examples only, and that the temperature of the process may vary depending upon the type of reactor employed, the type of catalyst used as well as other known factors. The pressure for the hydrolysis reaction is not particularly limited and is usually selected within a range of approximately atmospheric pressure to 1 MPa.

Of particular advantage, the present invention provides 1,4-HAB as a starting material or reactant. As discussed above, very large amounts of $H_2O$ are supplied to the reactor(s), i.e. in great stoichiometric excess. Of significant advantage, the method and system of the present invention serves to reduce the amount of $H_2O$ necessary to carry out the hydrolysis reaction. Suitable concentrations of the starting materials or reactants according to the method and system of the present invention are generally supplied to the reactor such that the weight percent ratio of 1,4-HAB to 1,4-BG at the outlet of the final reactor is in the recited range of 0.4 to 2.0, and the conditions of equations 1 through 7 are met. In FIG. 5a the outlet of the final, and only, reactor 42 is at pint 49. Such reactant concentrations can be easily calculated using known material balance calculations given the recited range information, equations and the equilibrium constants disclosed above. The concentration of 1,4-HAB in the feed stream, will vary depending on the type of reaction system configuration used. The inventors have found based on experimental data and simulations according to the method and system of the present invention, that the addition of 1,4-HAB to the reactor at a mass flow rate of about 1 kg/hr, reduces the usage of $H_2O$ by a mass flow rate of about 28 kg/hr at the condition where the 1,4-BG/1,4-HAB product ratio (i.e. at the final product outlet stream 55 of the system) is approximately 3.5. As mentioned above, reducing the usage of $H_2O$ has significant advantages, which include but are not limited to: lowering the energy consumption of the process; reducing the residence time of the reaction; and since $H_2O$ is typically provided in large stoichiometric excess, reducing the amount of $H_2O$ can allow a smaller reactor to be used. In summary, the inventors have found that no matter what type of reactor configuration is used, changing the starting materials or reactants from pure 1,4-DAB to a mixture of 1,4-DAB and 1,4-HAB according to the invention will provide significant advantages.

When employing a recycle stream to supply at least a portion, or optionally all, of the 1,4-HAB to the reactor, the composition of the recycle stream is generally comprised of both 1,4-HAB and unreacted 1,4-DAB. The concentration of components in the recycle streams will vary, and are dependent upon the system configuration and operating conditions. In one exemplary illustration, the recycle stream is comprised of approximately, in weight percent, 85 % 1,4-HAB, 14% 1,4-BG and 1% 1,4-DAB. The ratio of 1,4-HAB to 1,4-BG in the recycle stream is in the range of approximately 5:1 to 7:1. Referring again to FIGS. 5a and 5b, preferably a portion of 1,4-HAB is separated in second distillation tower 48 from the final product stream 55 and recycled to the reactor via recycle stream 45. Ideally the portion of 1,4-HAB separated in the second distillation tower 48 is 100%, that is pure 1,4-HAB without any 1,4-BG. However, large amounts of energy as well as capital expenditures are needed to remove all the 1,4-BG from 1,4-HAB in the recycle stream 45. Balancing the capital and energy cost, a preferred value of about 5:1 to 7:1 of 1,4-HAB to 1,4-BG was obtained. Of course, if other economical separation methodology can be established, pure 1,4-HAB in the recycle stream 45 will be more desirable. Preferably, distillation is used to separate 1,4-HAB from the product stream to produce the recycle stream containing 1,4-HAB.

Experimental

A number of experiments were performed to illustrate the advantages and features of the present invention. These experiments are offered for illustration purposes only and are not intended to limit the invention in any way.

Figure 7:
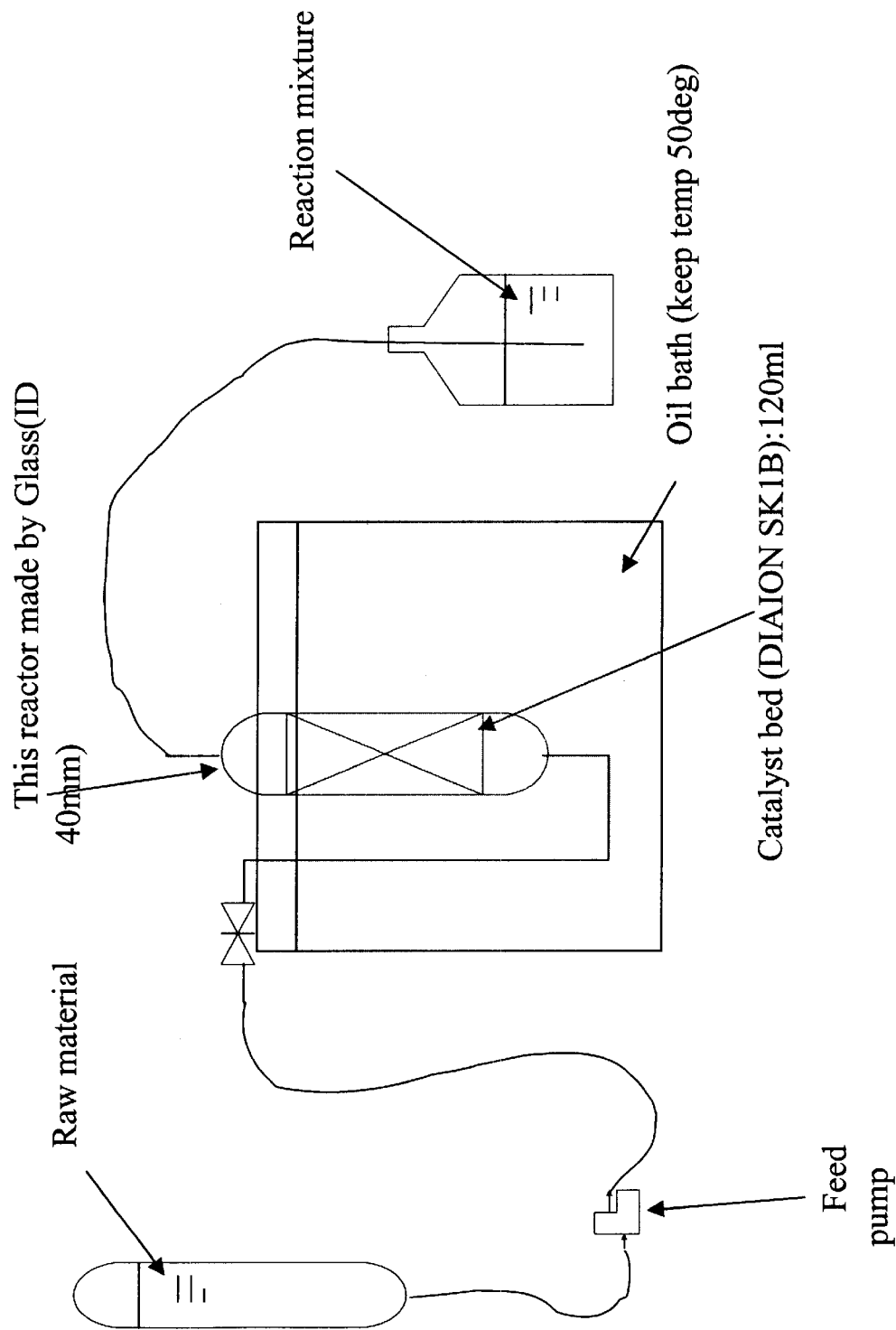
FIG. 7 is a schematic diagram of the experimental apparatus used to conduct pilot experiments in accordance with the present invention.

Pilot tests were run employing the system and method of the present invention. Experimental apparatus as shown in FIG. 7 was used to conduct the pilot tests. A reactor 70 made by Glass (ID=40 mm) having a catalyst bed 72 was used. The reactor 70 was placed in an oil bath 74 maintained at 50° C. The raw materials were mixed in tank 76 and fed via a feed pump 78 through the oil bath 74 and to the bottom of the reactor 70. The hydrolysis reaction was carried out at 50° C. The catalyst employed was DIAION® (Mitsubishi Chemical Corporation) (120 ml). The raw material flow rates were in the range of 30 to 240 ml/hr. As the reaction was carried out, the reaction mixture was collected in a tank 80, and the outlet composition was determined. Simulated results were calculated, and then actual results were obtained. The results are shown in Table 2 below:

TABLE 2

| Component | Inlet Composition (wt %.) | Outlet Composition simulated (wt %) | Outlet Composition actual (wt %) |
|---|---|---|---|
| $H_2O$ | 31.18 | 25.83 | 26.41 |
| Acetic Acid | 0.92 | 17.89 | 18.34 |
| THF | 0.00 | 0.03 | 0.11 |
| 1,4-DAB | 37.11 | 12.24 | 11.52 |
| 1,4-HAB | 26.77 | 29.15 | 28.08 |
| 1,4-BG | 4.01 | 14.85 | 15.54 |
| Reaction time (hrs) | — | 2.9 | 3.0 |
| Reaction constant k1 | — | 0.652 | 0.670 |
| Reaction constant k2 | — | 0.155 | 0.169 |
| k1/k2 | — | 4.21 | 3.96 |

As shown in Table 2, the simulated and actual results are comparable. Additional experiments were conducted as above, and actual results were obtained as shown in Tables 3–6 below:

TABLE 3

| Component | Inlet Composition (wt %.) | Outlet Composition simulated (wt %) | Outlet Composition actual (wt %) |
|---|---|---|---|
| THF | 0.003 | — | 0.031 |
| AcOH | 14.470 | — | 31.514 |
| 12DAB | 4.333 | — | 1.205 |
| 12HAB | 2.092 | — | 2.267 |
| 12BG | 0.632 | — | 1.867 |
| 14DAB | 44.037 | — | 14.918 |
| 14HAB | 6.096 | — | 18.417 |
| 14BG | 0.906 | — | 4.627 |
| H2O | 27.431 | — | 25.155 |
| Reaction time (hrs) | — | — | 3.96 |
| Reaction constant k1 | — | 0.652 | 0.612 |
| Reaction constant k2 | — | 0.155 | 0.138 |
| k1/k2 | — | 4.02 | 4.43 |

TABLE 4

| Component | Inlet Composition (wt %.) | Outlet Composition Simulated (wt %) | Outlet Composition actual (wt %) |
|---|---|---|---|
| THF | 0.000 | — | 0.085 |
| AcOH | 0.403 | — | 14.653 |
| 12DAB | 1.743 | — | 0.331 |

TABLE 4-continued

| Component | Inlet Composition (wt %.) | Outlet Composition Simulated (wt %) | Outlet Composition actual (wt %) |
|---|---|---|---|
| 12HAB | 0.886 | — | 1.650 |
| 12BG | 3.771 | — | 3.888 |
| 14DAB | 18.443 | — | 6.773 |
| 14HAB | 34.961 | — | 24.561 |
| 14BG | 8.670 | — | 19.705 |
| H2O | 31.122 | — | 28.354 |
| Reaction time(hrs) | — | — | 4.12 |
| Reaction constant k1 | — | 0.652 | 0.741 |
| Reaction constant k2 | — | 0.155 | 0.182 |
| k1/k2 | — | 4.02 | 4.07 |

TABLE 5

| Component | Inlet Composition (wt %.) | Outlet Composition simulated (wt %) | Outlet Composition actual (wt %) |
|---|---|---|---|
| THF | 0.004 | — | 0.041 |
| AcOH | 15.497 | — | 32.187 |
| 12DAB | 4.897 | — | 1.613 |
| 12HAB | 2.426 | — | 3.224 |
| 12BG | 1.513 | — | 2.344 |
| 14DAB | 47.672 | — | 17.598 |
| 14HAB | 3.757 | — | 18.189 |
| 14BG | 0.231 | — | 4.147 |
| H2O | 24.004 | — | 20.659 |
| Reaction time(hrs) | — | — | 3.98 |
| Reaction constant k1 | — | 0.652 | 0.637 |
| Reaction constant k2 | — | 0.155 | 0.156 |
| k1/k2 | — | 4.07 | 4.08 |

TABLE 6

| Component | Inlet Composition (wt %.) | Outlet Composition simulated (wt %) | Outlet Composition actual (wt %) |
|---|---|---|---|
| THF | 0.005 | — | 0.075 |
| AcOH | 0.768 | — | 15.598 |
| 12DAB | 2.077 | — | 0.418 |
| 12HAB | 0.776 | — | 2.096 |
| 12BG | 5.286 | — | 4.780 |
| 14DAB | 22.726 | — | 6.610 |
| 14HAB | 28.455 | — | 23.079 |
| 14BG | 6.782 | — | 18.038 |
| H2O | 33.126 | — | 29.306 |
| Reaction time(hrs) | — | — | 4.00 |
| Reaction constant k1 | — | 0.652 | 0.735 |
| Reaction constant k2 | — | 0.155 | 0.183 |
| k1/k2 | — | 4.07 | 4.07 |

Tables 3 to 6 show good correlation between the reaction constants for the actual and simulated results.

Additional experiments were conducted using the one reactor stage system configuration as shown in FIG. 6a. Specifically, the following reactants were supplied to the reactor: 12,800 kg/hr 1,4-DAB, 26,050 kg/hr $H_2O$ and 4000 kg/hr 1,4-HAB . The hydrolysis reaction was carried out at a temperature and pressure of 50 degrees C and 0.3 Mpa (Gauge), for a period of hours. The reactor capacity was 730 l/min. The final product stream contained 966 kg/hr unreacted 1,4-DAB, 1009 kg/hr 1,4-HAB and 5434 kg/hr 1,4-BG.

Further experiments were conducted using the three reactor stage system configuration shown in FIG. 5b. In this example, the following reactants were added to the first reactor: 12,800 kg/hr 1,4-DAB, 8550 kg/hr $H_2O$ and 1000 kg/hr 1,4-HAB. The 1,4-HAB was recycled from the final distillation tower to the first reactor. $H_2O$ is additionally added, separately to the second and third reactors at a rate of 6050 kg/hr to each, to give a total amount of $H_2O$ consumed in the system to 20,650 kg/hr. Each of the three reactors have a capacity of 350 l/min, 260 l/min and 250 l/min, respectively. The final product streams contained 248 kg/hr 1,4-DAB, 2537 kg/hr 1,4-HAB and 5438 1,4-BG.

As taught by the foregoing description and examples, a greatly advanced method of producing 1,4-BG is provided by the method and system of the present invention. The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

We claim:

1. A method of producing 1,4-butanediol (1,4-BG) in a hydrolysis reaction, comprising the steps of:

supplying at least 1,4-diacetoxybutane (1,4-DAB), 1,4-hydroxyacetoxybutane (1,4-HAB), and water ($H_2O$) to at least one reactor;

reacting said 1,4-DAB, 1,4-HAB and $H_2O$ to produce an effluent stream comprising 1,4-BG, 1,4-HAB, $H_2O$ and acetic acid;

supplying said effluent stream to a separation system having at least one separator wherein said $H_2O$ and acetic acid are separated in a purge stream, and at least one product stream is produced comprising 1,4-HAB and 1,4-BG, wherein the following equations are satisfied:

$$Min \leq Var \leq Max$$

where $Max=(7.59D-0.76)/n$ $Min=(3.79D-2.00)/n$ $Var=B/A$ $D=174(C)/90(A)$ and where A is the feed rate of 1,4-DAB to the reaction system in kg/hr;

B is the feed rate of fresh 1,4-HAB to the reaction system plus the total amount of 1,4-HAB recycled to the reaction system in kg/hr;

C is the amount of 1,4-BG produced by the reaction system, and n is the number of reactors within the reaction system; and wherein the one or more product stream is substantially comprised of 1,4-BG.

2. The method of claim 1 wherein the 1,4-HAB is supplied to said one or more reactor by one or both of the following steps: supplying 1,4-HAB as a feed to said one or more reactor, or supplying 1,4-HAB by recycling at least a portion of said 1,4-HAB from said effluent stream to said one or more reactor.

3. The method of claim 1 wherein the recycled 1,4-HAB reacts in said reactor and shifts the equilibrium of the hydrolysis reaction such that the amount of $H_2O$ needed for the hydrolysis reaction is reduced as compared to that amount of $H_2O$ needed in the absence the 1,4-HAB supplied to the reactor.

4. The method of claim 1 wherein the following equations are satisfied:

$Min' \leq Var \leq Max$ where $Max=(7.59D-0.76)/n$ $Min'=(3.79D-1.46)/n$ $Var=B/A$ $D=174(C)/90(A)$ and where A is the feed rate of 1,4-DAB to the reaction system in kg/hr;

B is the feed rate of fresh 1,4-HAB to the reaction system plus the total amount of 1,4-HAB recycled to the reaction system in kg/hr;

C is the amount of 1,4-BG produced by the reaction system, and n is the number of reactors within the reaction system.

5. The method of claim 1 wherein said method is carried out in one reactor/separator.

6. The method of claim 1 wherein the portion of 1,4-HAB recycled to said one or more reactor has a concentration ratio in weight percent of 1,4-HAB to 1,4-BG in the range of about 5:1 to 7:1.

7. The method of claim 3 wherein a water efficiency of the hydrolysis reaction is defined as the amount of 1,4-BG produced divided by the total amount of $H_2O$ consumed in the hydrolysis reaction, and wherein the water efficiency is two or more times greater than the water efficiency when no 1,4-HAB is supplied to the reactor.

8. The method of claim 7 wherein the water efficiency is about three times greater than the water efficiency when no 1,4-HAB is supplied to the reactor.

9. A method of increasing the production of butanediol in a hydrolysis reaction system characterized in that reactants 1,4-diacetoxybutane (1,4-DAB), 1,4-hydroxyacetoxybutane (1,4-HAB) and water ($H_2O$) are reacted in a reactor to produce an effluent stream comprising substantially 1,4-butanediol (1,4-BG) and 1,4-HAB wherein the following equations are satisfied:

$$Min \leq Var \leq Max$$

where $Max=(7.59D-0.76)/n$ $Min=(3.79D-2.00)/n$ $Var=B/A$ $D=174(C)/90(A)$ and where A is the feed rate of 1,4-DAB to the reaction system in kg/hr;

B is the feed rate of fresh 1,4-HAB to the reaction system plus the total amount of 1,4-HAB recycled to the reaction system in kg/hr;

C is the amount of 1,4-BG produced by the reaction system, and n is the number of reactors within the reaction system.

10. The method of claim 9 wherein the following equations are satisfied:

$Min' \leq Var \leq Max$ where $Max=(7.59D-0.76)/n$ $Min'=(3.79D-1.46)/n$ $Var=B/A$ $D=174(C)/90(A)$ and where A is the feed rate of 1,4-DAB to the reaction system in kg/hr;

B is the feed rate of fresh 1,4-HAB to the reaction system plus the total amount of 1,4-HAB recycled to the reaction system in kg/hr;

C is the amount of 1,4-BG produced by the reaction system, and n is the number of reactors within the reaction system.

11. The method of claim 9 wherein the ratio of 1,4-HAB to 1,4-BG at the outlet of the last reactor of the reaction system is in the range of about 0.4 to 2.0.

12. The method of claim 9 wherein the hydrolysis reaction is carried out in one reactor stage.

13. The method of claim 9 wherein 1,4-HAB is provided by at least partially separating 1,4-HAB from said product stream and recycling the 1,4-HAB back to the reactor.

14. The method of claim 9 wherein the hydrolysis reaction is carried out in two or three reactor stages.

15. The method of claim 9 wherein a water efficiency of the hydrolysis reaction is defined as the amount of 1,4-BG produced divided by the total amount of $H_2O$ consumed in the hydrolysis reaction, and wherein the water efficiency is two or more times greater than the water efficiency when no 1,4-HAB is supplied to the reactor.

16. The method of claim 15 wherein the water efficiency is about three times greater than the water efficiency when no 1,4-HAB is supplied to the reactor.

17. The method of claim 13 wherein the portion of 1,4-HAB recycled to said one or more reactor has a concentration in weight percent of 1,4-HAB to 1,4-BG in the range of about 5:1 to 7:1.

* * * * *